US012746072B2

(12) United States Patent
Hengerer

(10) Patent No.: US 12,746,072 B2
(45) Date of Patent: Sep. 29, 2026

(54) MAGNETIC RESONANCE IMAGING DEVICE AND METHOD FOR POSITIONING A MEDICAL INSTRUMENT

(71) Applicant: Siemens Healthineers AG, Forchheim (DE)

(72) Inventor: Arne Hengerer, Möhrendorf (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 19/060,165

(22) Filed: Feb. 21, 2025

(65) Prior Publication Data

US 2025/0288362 A1 Sep. 18, 2025

(30) Foreign Application Priority Data

Mar. 12, 2024 (DE) ..................... 10 2024 202 289.6

(51) Int. Cl.
*A61B 34/20* (2016.01)
*A61B 34/00* (2016.01)
(Continued)

(52) U.S. Cl.
CPC .............. *A61B 34/20* (2016.02); *A61B 34/25* (2016.02); *A61B 90/08* (2016.02); *A61B 90/39* (2016.02);
(Continued)

(58) Field of Classification Search
CPC ............ A61B 2090/374; A61B 90/361; A61B 1/00045; A61B 34/25; A61B 90/08;
(Continued)

(56) References Cited

U.S. PATENT DOCUMENTS

| | | | | |
|---|---|---|---|---|
| 2012/0265051 A1* | 10/2012 | Fischer | .................. | A61B 34/37 73/800 |
| 2013/0021034 A1* | 1/2013 | Heismann | .............. | A61B 5/055 324/318 |

(Continued)

FOREIGN PATENT DOCUMENTS

| | | | | |
|---|---|---|---|---|
| EP | 4202467 A1 | 6/2023 | | |
| WO | WO-2022223323 A1 * | 10/2022 | ............. | A61B 5/165 |

OTHER PUBLICATIONS

Toshiba Corporation: Corporate Research & Development Center—Dec. 2015. pp. 1-4. Obtained: https://www.global.toshiba/ww/technology/corporate/rdc/rd/topics/15/1512-01.html.

*Primary Examiner* — Gerald Johnson
(74) *Attorney, Agent, or Firm* — Lempia Summerfield Katz LLC

(57) ABSTRACT

A magnetic resonance imaging device for an interventional procedure, a medical instrument, and a method for aligning the medical instrument in the magnetic resonance imaging device are disclosed. The magnetic resonance imaging device has a recess along an inner circumference of a patient tunnel and a display arranged therein. The medical instrument has an optical image capturing apparatus at the distal end. In the method, a trajectory for the medical instrument is ascertained for a predetermined interventional procedure in a patient, an entry point on the patient and an impact point of the trajectory on the display are determined, the medical instrument is positioned at the entry point by a user, the impact point is marked by outputting a marking on the display, and the distal end of the medical instrument is aligned with the marking.

15 Claims, 3 Drawing Sheets

(51) Int. Cl.

| | |
|---|---|
| ***A61B 90/00*** | (2016.01) |
| *A61B 10/02* | (2006.01) |
| *A61N 5/10* | (2006.01) |

(52) U.S. Cl.
CPC ... *A61B 10/0233* (2013.01); *A61B 2034/2051* (2016.02); *A61B 2090/374* (2016.02); *A61B 2090/3945* (2016.02); *A61N 5/1007* (2013.01)

(58) Field of Classification Search
CPC ........ A61B 10/0233; A61B 2034/2068; A61B 2034/2051; A61B 90/39
See application file for complete search history.

(56) References Cited

U.S. PATENT DOCUMENTS

| | | | | |
|---|---|---|---|---|
| 2014/0303483 | A1 * | 10/2014 | Schellenberg ........... | A61B 6/12<br>600/411 |
| 2021/0274152 | A1 * | 9/2021 | Ziarati ................. | H04N 13/302 |
| 2023/0200912 | A1 | 6/2023 | Hengerer | |
| 2024/0277324 | A1 * | 8/2024 | Yuen ...................... | A61B 34/37 |

* cited by examiner

MAGNETIC RESONANCE IMAGING DEVICE AND METHOD FOR POSITIONING A MEDICAL INSTRUMENT

The present patent document claims the benefit of German Patent Application No. 10 2024 202 289.6, filed Mar. 12, 2024, which is hereby incorporated by reference in its entirety.

TECHNICAL FIELD

The disclosure relates to a magnetic resonance imaging device, a medical instrument for use in a magnetic resonance imaging device, and a method for positioning a medical instrument as claimed in one of the claims on a patient. The magnetic resonance imaging device has a display in the patient tunnel. The medical instrument has an image capturing facility. A trajectory for the medical instrument is ascertained for a predetermined procedure, the instrument is positioned on the patient and aligned by a marking on the display.

BACKGROUND

Image-guided minimally invasive procedures are also performed in magnetic resonance imaging devices. For this purpose, the medical instrument is propagated through the magnetic resonance imaging device under real-time control. This requires the instrument for placement to be positioned in a predetermined alignment on the insertion point before being inserted into the abdomen or pelvic region of the patient. Herein, the outcome of the procedure or procedures during the course of a working day depends on many factors. In particular, herein, the interaction between the surgeon and the individual components provides a lasting outcome.

The entry point and alignment may be planned in the patient's anatomical magnetic resonance image. The advancement of the needle is visualized using real-time magnetic resonance imaging.

The insertion angles in two spatial directions are estimated, e.g., by the person performing the intervention placing a finger on the insertion point and correcting the alignment of a finger in the MRI image until it is estimated to be in the correct position.

SUMMARY AND DESCRIPTION

It is therefore an object of the disclosure to provide a medical instrument and a method that facilitates and improves alignment.

The object is achieved by a magnetic resonance imaging device, a medical instrument, and a method for positioning a medical instrument in an interventional procedure as described herein. The scope of the present disclosure is defined solely by the appended claims and is not affected to any degree by the statements within this summary. The present embodiments may obviate one or more of the drawbacks or limitations in the related art.

The magnetic resonance imaging device is provided for an interventional procedure. In certain examples, the magnetic resonance imaging device provides a user or surgeon with good access to a patient. The magnetic resonance imaging device has a field magnet with a patient tunnel for receiving a patient. The patient tunnel may be arranged horizontally through the cryostat of the field magnet, parallel to the field lines of the magnet.

The patient tunnel at least partially has a recess radially outward along a circumferential direction. In other words, a recess is arranged in the inner wall of the patient tunnel, wherein the recess extends at least partially along a circumferential direction of the patient tunnel. A display is arranged in the recess along the circumferential direction. The display may extend by at least 5 degrees, 15 degrees, 30 degrees, 45 degrees, 60 degrees, or 90 degrees of a circumferential angle of the inner circumference. In certain examples, the display extends in the longitudinal direction of the patient tunnel from an impact point on the patient by an opening angle by at least 5 degrees, 15 degrees, 30 degrees, or 45 degrees. In other words, when viewed from the impact point, the display appears at a corresponding angle, so that an inclination of a medical instrument in a corresponding angular range may be defined by a marking on the display.

Herein, the recess may be a depression or pocket in the wall of the patient tunnel and thus the wall of the patient tunnel may continue to have a closed surface behind the display without an opening. However, in an alternative example, the recess is an opening or hole in the wall of the patient tunnel in which the display is arranged. The recess may be regarded as a volume that is free for the display, so that a display arranged therein does not protrude toward the patient compared to sections of the wall of the patient tunnel adjacent to the recess in a longitudinal direction of the patient tunnel. The recess may be covered toward the patient by a transparent window through which the display remains visible from inside the patient tunnel.

Advantageously, the display in a depression allows flexible positioning of a marking for aligning a medical instrument without any loss of width of the patient tunnel.

The medical instrument disclosed herein is a medical instrument for an interventional procedure. The medical instrument extends in a longitudinal direction. In other words, the medical instrument has an elongate shape, the largest dimension of which is along the longitudinal direction and is larger than the measurements in the other dimensions, for example, by a factor of at least 5 or 10. The medical instrument may be a biopsy needle or another instrument for a minimally invasive procedure.

When used appropriately for the application, the medical instrument has a proximal end and a distal end along the longitudinal direction of the medical instrument, wherein the proximal end is configured to be positioned on or in the course of the procedure in the patient and the distal end is configured to remain outside the patient for handling or guidance by a surgeon or user. An optical image capturing apparatus, for example, a camera or scanner, is arranged at the distal end of the medical instrument in order to perform optical image capture, wherein 'optical' is not limited to the immediately visible frequency range but may also include infrared or ultraviolet wavelengths. The image capture is designed, in a position appropriate for the application, e.g., with the proximal end at an entry point on the patient and with the distal end facing away from the patient aligned along a trajectory for a procedure on the patient, to capture a display on an inner wall of a magnetic resonance imaging device in a map. The image capturing apparatus may be aligned parallel to the longitudinal direction, with a capture direction away from the patient in continuation of a direction from the proximal end to the distal end, away from the patient.

Advantageously, the image capturing apparatus enables the medical instrument to be aligned with a marking in the patient tunnel without a direct view of the user.

The method is provided for positioning a medical instrument on a patient in a patient tunnel of a magnetic resonance imaging device. The medical instrument extends in a longitudinal direction. In other words, the medical instrument has an elongate shape, the largest dimension of which is along the longitudinal direction and is greater than the measurements in the other dimensions, for example, by a factor of at least 5 or 10. When used appropriately for the application, the medical instrument has a proximal end and a distal end along the longitudinal direction of the medical instrument, wherein the proximal end is configured to be positioned on or in the course of the procedure in the patient and the distal end is configured to remain outside the patient for handling or guidance by a surgeon or user. The patient tunnel at least partially has a recess along an inner circumference. In other words, a recess is arranged in the inner wall of the patient tunnel, wherein the recess extends at least partially along an inner circumference of the patient tunnel. A display is arranged in the recess along the inner circumference. The statements already made relating to the recess and the display apply here.

In one act of the method, a trajectory for the medical instrument is ascertained for a predetermined procedure. This may be done by controlling the magnetic resonance imaging device or a planning system by magnetic resonance mapping of the patient and information about the target of the medical instrument in the procedure, which is specified by a user or the planning system. Herein, the trajectory is a straight line through an entry point on the surface of the patient to the target, avoiding sensitive organs or structures such as nerves and larger blood vessels or obstacles such as bones.

In a further act, the entry point is identified according to the trajectory relative to the patient and an alignment of the medical instrument is determined that enables movement of the medical instrument along the trajectory. Herein, 'identify' may be understood as meaning that the entry point of the trajectory which was determined on the image or model of the patient is assigned to the real patient and may be marked. An alignment corresponding to the ascertained trajectory is also ascertained, e.g., by the controller of the magnetic resonance imaging device. This may be done in that a magnetic resonance image of the patient is captured by the magnetic resonance imaging device and a position of the patient is captured based on the contour and or organs relative to the magnetic resonance imaging device. From this position, the controller may determine a coordinate transformation that transforms the coordinates of the model to the real position of the patient in the magnetic resonance imaging device when ascertaining the trajectory. Applying this coordinate transformation to the ascertained entry point and the alignment of the medical instrument obtains the entry point and the alignment on the real patient in the magnetic resonance imaging device.

In a further act, the user positions the medical instrument at the entry point on the patient. Herein, it is conceivable that, for this purpose, the magnetic resonance imaging device captures the patient with the medical instrument or a marker on a tip of the medical instrument facing the patient and outputs the position of the ascertained entry point and the position of the tip to the user, for example, in a graphical representation, as coordinates or a coordinate difference or in the form of an indication of a direction of movement for the instrument to reach the entry point.

In another act, the controller marks the impact point by outputting a marking on the display. The marking on the display may be a dot, a flashing dot, a target circle, or a concentric pattern, as is the case with a target or crosshair.

In a further act, the user or surgeon aligns the distal end with the marking on the display. In certain examples, this may be done by the user aligning an aiming apparatus arranged on the medical instrument with the marking on the display by tilting the medical instrument to bring it into coincidence with the marking on the display.

Advantageously, the method provides convenient and precise alignment of the medical instrument.

In one embodiment of the method, the magnetic resonance imaging device has a gradient coil that is divided into a first section and a second section. The patient tunnel of the magnetic resonance imaging device extends in an axial direction through which the patient is moved into the patient tunnel. The axial direction of the patient tunnel may be parallel to a field direction of a field magnet for providing the static magnetic field B0. The first section and the second section of the gradient coil are arranged adjacent along the patient tunnel in the axial direction at a distance from one another, so that a recess or cutout is provided between the first section and the second section of the gradient coil, wherein the recess or cutout recedes radially outward in the wall of the patient tunnel. The recess extends at least around a part of the inner circumference of the patient tunnel, for example, by a circumferential angle that is at least 5 degrees, 15 degrees, 30 degrees, 45 degrees, 60 degrees, or 90 degrees. An extension of the recess in the longitudinal direction of the patient tunnel may be at least 5 cm, 15 cm, 30 cm, or 50 cm. The extension may also correspond to a viewing angle or opening angle from a position on an axis of symmetry in a center of a circumferential circle through the recess in the middle of the patient tunnel. The viewing or opening angle may be at least 5 degrees, 15 degrees, 30 degrees, or 45 degrees. The first section and the second section may be connected to one another by electrical lines so that they interact when the gradient fields are generated. It is, for example, conceivable to connect the first section and the second section in parallel or in series.

Advantageously, the gradient coil that is mechanically divided into two sections enables a recess to be provided between the sections near the field of view which may accommodate a display without reducing the usable inner circumference of the patient tunnel.

In one embodiment of the magnetic resonance imaging device, the display has electromagnetic shielding in order to reduce interference with the magnetic resonance signals caused by emissions of the display and/or interference with the display caused by magnetic and/or electromagnetic fields during the magnetic resonance mapping. The shielding may be made of metal, e.g., in the form of a perforated or slotted grid in the direction of the interior of the patient tunnel, so that a representation on the display remains visible from the patient tunnel. The interruption of the metal surface, in particular by slots, may also advantageously reduce interference caused by induced eddy currents. Frequency-selective shielding that reduces the influence of the shielding on relevant frequency ranges of the magnetic resonance signal are also conceivable.

The shielding advantageously reduces mutual interference between the magnetic resonance imaging device and the display.

In one possible embodiment of the method, a medical instrument is used that, as already explained, extends in a longitudinal direction, wherein an optical image capturing apparatus is provided at the distal end of the medical instrument that is configured, when the medical instrument is positioned appropriately for the application, to capture the display at least partially in the recess of the magnetic resonance imaging device in a map when the medical instrument is aligned with the patient. The optical image capturing apparatus may be a camera. Herein, by tilting the medical instrument, the user brings the marking on the display to a predetermined position in a map captured by the image capturing apparatus. For example, the controller may superimpose frames or markers in the map to indicate the predetermined position, so that the user only has to bridge the displayed marking into a predetermined position in relation to the frame. For example, the marking may be a dot or small circular area that is brought into coincidence with a ring.

Advantageously, the camera may also be used without looking directly at the medical instrument and/or the display.

In another embodiment of the method, a medical instrument with a luminous pointer is used. The luminous pointer projects a light marking or marker along the elongate shape or longitudinal direction of the medical instrument in the distal direction. In the act of aligning the distal end, the user, looking directly at the light marking or marker of the luminous pointer, brings it into coincidence with the marking on the display by changing the inclination of the medical instrument.

Advantageously, the luminous pointer may be realized with inexpensive and simple means and interferes less with the image capture of the magnetic resonance imaging device.

The above-described properties, features, and advantages of the disclosure and the manner in which they are achieved become clearer and more comprehensible in conjunction with the following description of the embodiments explained in more detail in conjunction with the drawings.

DETAILED DESCRIPTION

Figure 1:
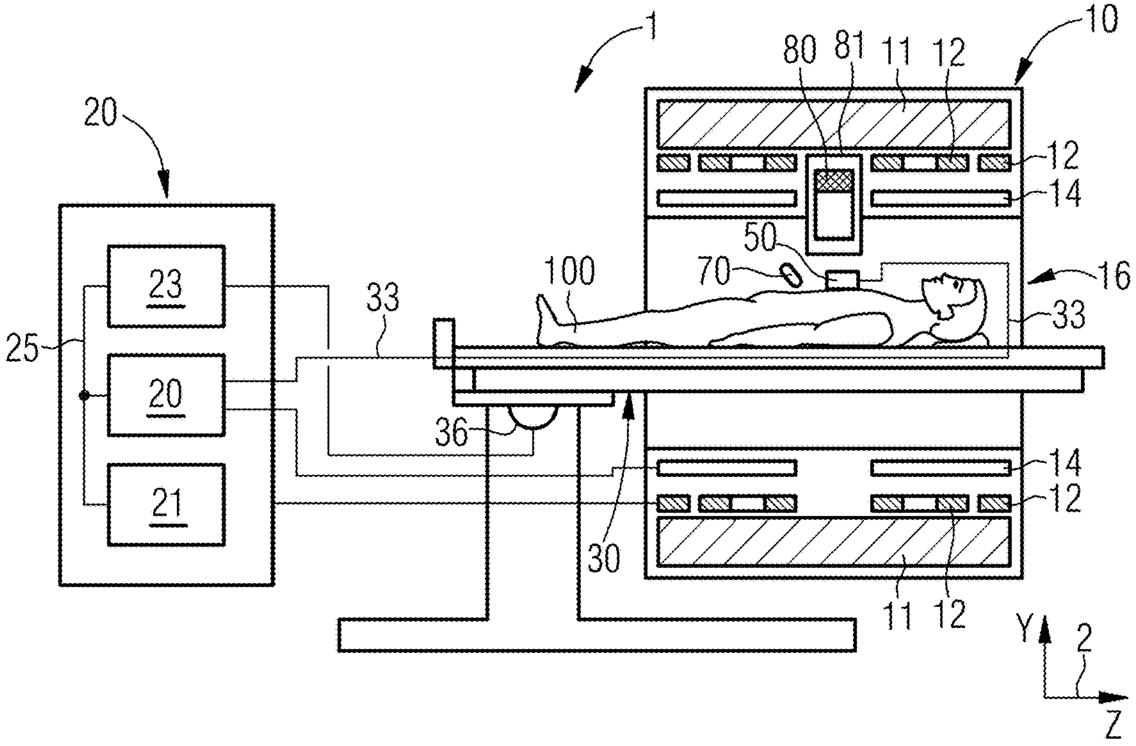
FIG. 1 depicts a schematic representation of an example of a magnetic resonance imaging device.

FIG. 1 shows a schematic representation of an embodiment of a magnetic resonance imaging device 1 for carrying out the method with the medical instrument 70.

The magnet unit 10 has a field magnet 11 that generates a static magnetic field B0 for aligning nuclear spins of samples or the patient 100 in a receiving region. The receiving region is characterized by an extremely homogeneous static magnetic field B0, wherein the homogeneity in particular relates to the magnetic field strength or the absolute value. The receiving region is almost spherical and is arranged in a patient tunnel 16, which extends in a longitudinal direction 2 through the magnet unit 10.

A patient couch 30 may be moved in the patient tunnel 16 by the positioning unit 36.

The field magnet 11 may be a superconducting magnet configured to provide magnetic fields with a magnetic flux density of up to 3 T or even higher. However, permanent magnets or electromagnets with normally conducting coils may also be used for lower field strengths.

Furthermore, the magnet unit 10 has gradient coils 12 configured to overlay the magnetic field B0 with variable magnetic fields in three spatial directions for the purpose of spatially differentiating the captured mapping regions in the examination volume. The gradient coils 12 may be coils made from normally conductive wires that may generate mutually orthogonal fields in the examination volume.

The magnet unit 10 also has a body coil 14 configured to radiate a radio-frequency signal supplied via a signal line into the examination volume and to receive resonance signals emitted by the patient 100 and emit them via a signal line. Hereinafter, the term ‘transmitting antenna’ refers to an antenna via which the radio frequency signal is emitted to excite the nuclear spins. This may be the body coil 14 or a local coil 50 with a transmitting function.

The patient tunnel 16 has a recess 81 that extends at least partially along an inner circumference of the patient tunnel. In certain examples, the recess extends at least partially along a circumferential angle from which an instrument 70 may access the patient 100. In particular, the recess 81 extends in the inner wall of the patient tunnel 16 opposite a side of the patient 100 facing away from the couch 30, i.e., above the patient tunnel 16. The recess extends along a plane that is perpendicular to the z-direction 2 or longitudinal axis of the patient tunnel. In the axial direction, along the z-axis 2, the width of the recess 81 may be at least 10 cm, 20 cm, or 40 cm. In the radial direction, the depth of the recess relative to an adjacent wall of the patient tunnel 16 is at least such that a display 80 may be arranged in the recess, which is flat relative to the inner wall of the patient tunnel 16 or recedes relative thereto.

In order to be able to provide the recess on the inner wall of the patient tunnel 16, the gradient coil 12 and/or the body coil 14 may be divided in the longitudinal direction 2 or z-direction into at least 2 parts, which are spaced apart from one another along the longitudinal direction 2 such that the recess 81 may be arranged therebetween.

The display 80 is arranged in the recess 81 such that the display 80 is flush with the adjacent wall of the patient tunnel 16 or offset radially outward, i.e., recedes therefrom. The display 80 may be curved so that the display may follow the course of the curvature along the inner circumference of the patient tunnel 16 without protruding out of the recess 81. Alternatively, the display 80 may be flat if the extension along the circumferential angle is small enough or the recess is deep enough in the radial direction.

Herein, the recess 81 may also be larger than the display 80, in particular also in the direction of the circumferential angle. Herein, the position of the display 80 in the recess 81 may be changed. For example, a rail may be provided in the recess along which the display 80 may be brought into a predetermined position in the recess. A motorized adjustment and/or a position sensor with which a controller 23 of the magnetic resonance imaging device may determine the position of the display 80, in particular along the circumferential angle.

A control unit 20 supplies the magnet unit 10 with the various signals for the gradient coils 12 and the body coil 14 and evaluates the received signals.

Thus, the control unit 20 has a gradient controller 21 configured to supply the gradient coils 12 via supply lines with variable currents that provide the desired gradient fields in the examination volume in a time-coordinated manner.

Furthermore, the control unit 20 has a radio-frequency unit 22 that is configured to generate a radio-frequency pulse having a predetermined time profile, amplitude, and spectral power distribution for exciting a magnetic resonance of the nuclear spins in the patient 100. Herein, pulse powers in the kilowatt range may be achieved. The excitation signals may be radiated into the patient 100 via the body coil 14 or also via a local transmitting antenna.

A controller 23 communicates with the gradient controller 21 and the radio-frequency unit 22 via a signal bus 25.

A local coil 50 is arranged on the patient 100 and is connected to the radio-frequency unit 22 and its receiver via a connecting line 33. However, in an alternative embodiment, the body coil 14 may be a receiving antenna.

A surgeon arranges the medical instrument 70 appropriately for the application on the patient 100 in the patient tunnel 16 in the capturing region of the magnetic resonance imaging device 1. The medical instrument 70 may be a biopsy needle, an instrument for brachytherapy, or another instrument configured to be introduced into the body of the patient 100 in the course of an interventional procedure. For this purpose, the medical instrument 70 is placed at a predetermined entry point on the surface or skin of the patient 100 and aligned according to a predetermined inclination along a trajectory to a target location in the body of the patient 100.

Figure 2:
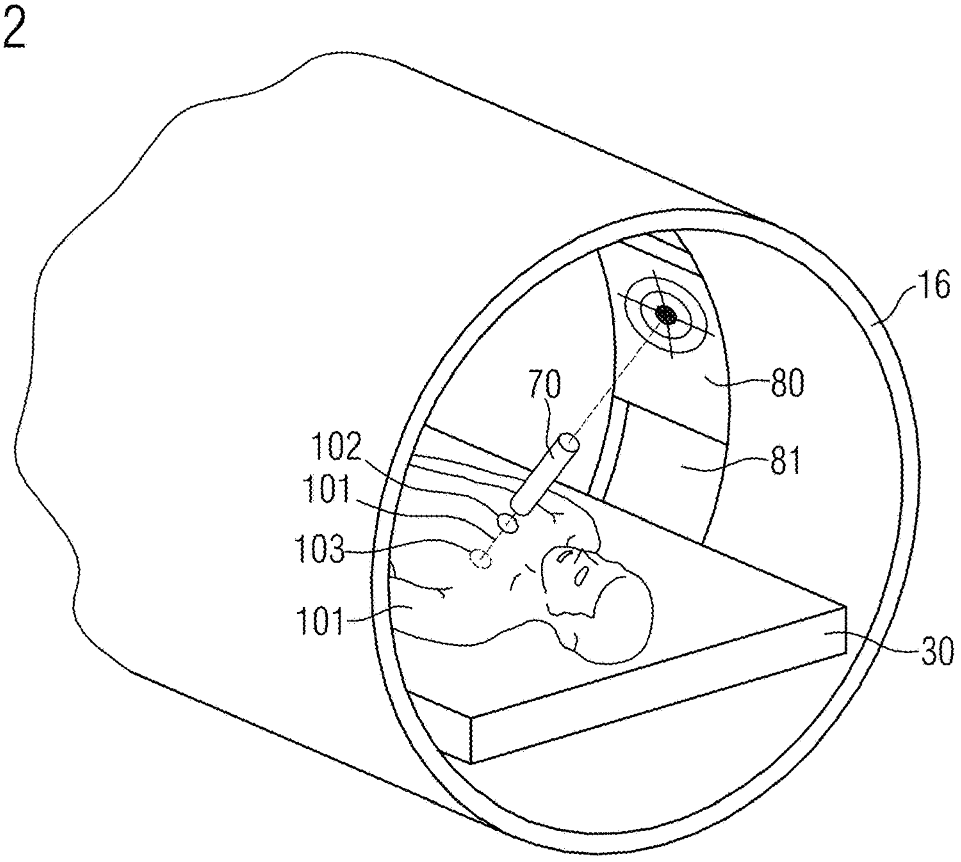
FIG. 2 depicts a schematic representation of an embodiment of a magnetic resonance imaging device with a medical instrument.

FIG. 2 shows a detail of an embodiment of the magnetic resonance imaging device 1 in FIG. 1.

A target point 103 is predetermined in the patient, for example, a node that has been identified in a map of the patient 100 with its coordinates. A medical instrument 70, for example, a biopsy needle with which a sample is to be taken from the target object at the target point 103, is placed at an entry point on the surface of the patient, which is identified by a marking 102. The marking may also be visible in a magnetic resonance image. However, a marking 102 is also conceivable solely by the impression of the instrument 70 in the patient 100, which is also visible in the magnetic resonance image. A trajectory 101, (a straight line), connects the entry point and the target point 103, wherein the trajectory may be selected such that the trajectory does not hit any important organ, blood vessel, nerve, or other tissue to be protected.

The predetermined trajectory 101 has a point of intersection with the patient tunnel 16 or its inner wall on a side facing away from the patient 100. This point of intersection may be calculated using the methods of linear algebra if the relative position of the patient 100 to the magnetic resonance imaging device 1 is known. One possibility for determining the trajectory 101 and point of intersection is a magnetic resonance recording of the patient 100 in which the target object 103 and the planned entry point are visible.

The point of intersection calculated, for example, by the controller 23 is output on the display 80 in the form of a pattern, for example, a crosshair, which identifies the point of intersection.

To do this, the position of the display 80 is known to the controller 23. This may be fixed and defined during construction so that the position is stored in the controller 23. In the case of a display 80 that may be moved in the recess 81 along the inner circumference, the controller 23 may capture information on the position, for example, by user input, for example, by notches or markings being applied and identified along the circumference and the user reading and inputting the notch position. However, the controller 23 may also capture the position directly, for example, by position sensors or by a motor control for moving the display 80 along the recess 81.

The controller may then output the marking on the display 80 at the position corresponding to the point of intersection.

Figure 3:
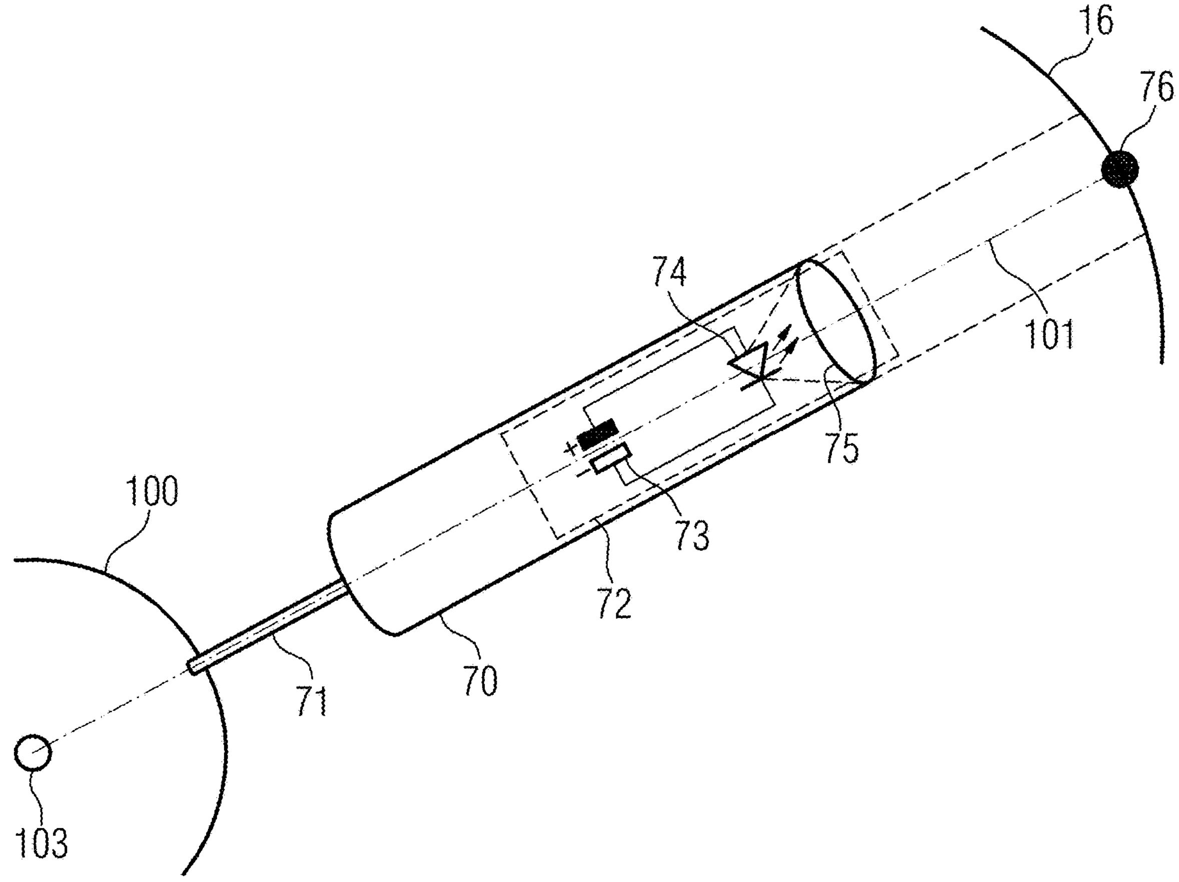
FIG. 3 depicts a schematic representation of an embodiment of a medical instrument.

FIG. 3 is a schematic representation of an embodiment of the medical instrument 70. The geometric explanations also apply to an instrument as shown below in FIG. 4. The medical instrument 70 has an axis of symmetry, which is defined here by the biopsy needle 71. The symmetry with respect to the axis of symmetry reflects a symmetry of the medical instrument 70 or the application to be performed therewith. In the case of the biopsy needle, this may be rotated about an axis of the hollow needle 71 during the application without further consequences. Accordingly, the axis of symmetry of the medical instrument 70 in FIG. 3 is an axis of rotation of the hollow needle 71. If this is brought into coincidence with the predetermined trajectory 101, the medical instrument 70 is correctly aligned with the target object 103.

For this purpose, the medical instrument 70 in FIG. 3 has a projector 72. The projector 72 has an energy source, for example, a battery 73. However, it is also conceivable that the energy source is a power supply line. The energy source supplies a light source, e.g., a semiconductor laser 74. However, light sources such as lamps or an OLED matrix are also conceivable. The generated light is bundled by an optical system 75 into a light beam that is emitted parallel to the axis of symmetry of the medical instrument 60 in a direction opposite to the patient 100. When the light beam strikes the display, the light beam generates a luminous point 76 in the form of a spot or dot, or as explained below, a more complex pattern. If the medical instrument 70 is arranged with the tip or the hollow needle 71 at the entry point arranged and the user aligns the luminous pointer 76 with the marking on the display 80, these two fixed points define a straight line, which corresponds to the predetermined trajectory 101 and provides that the medical instrument 70 is aligned.

Figure 4:
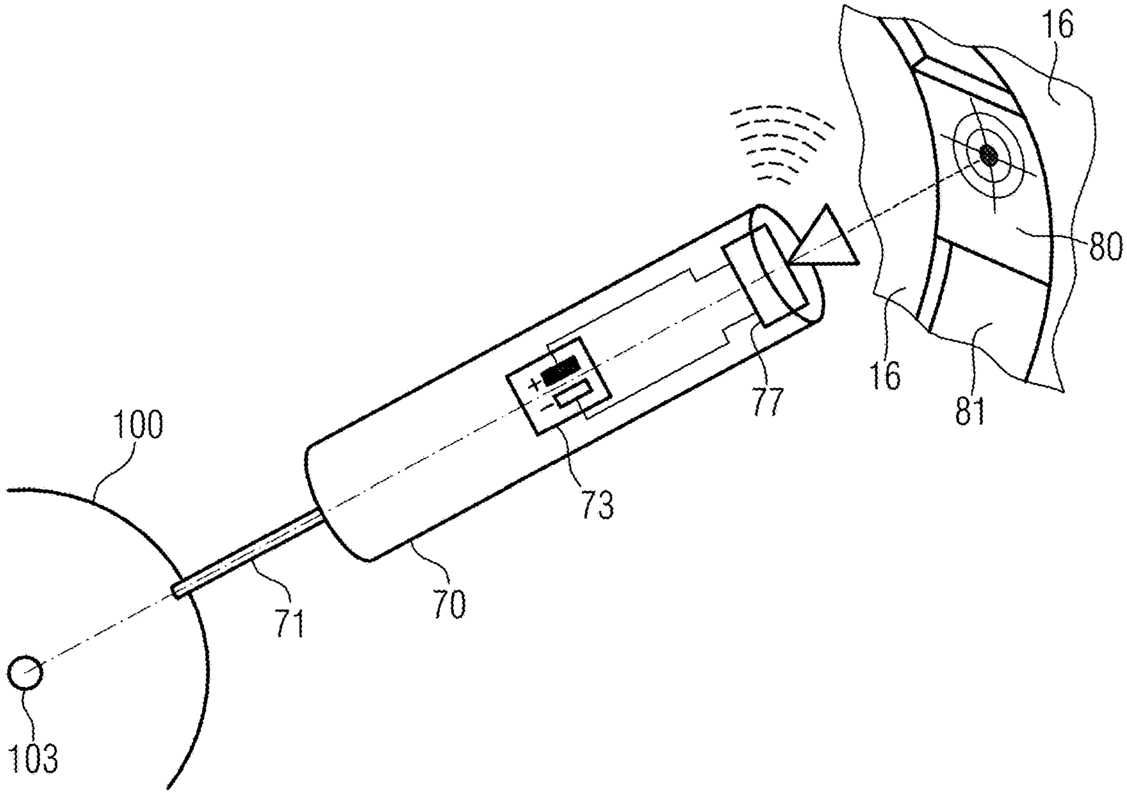
FIG. 4 depicts a schematic representation of an embodiment of a medical instrument.

FIG. 4 is a schematic representation of an embodiment of a medical instrument 70. The medical instrument has a camera 77 that captures an image centered on the axis of rotation of the medical instrument 70, but opposite to the alignment on the patient 100. The camera 77 may transmit the image signal wirelessly and may be powered by a battery 73.

If the surgeon positions the medical instrument 70 with the hollow needle 71 at the entry point, the surgeon may change the inclination of the medical instrument 70 until the marking output on the display 80 is centered on the image captured by the camera, which is, for example, shown to the surgeon on a display outside the patient tunnel 16.

Advantageously, this enables the alignment along the trajectory 101 to be achieved without the surgeon having a direct view of the inner wall of the patient tunnel 16.

Figure 5:
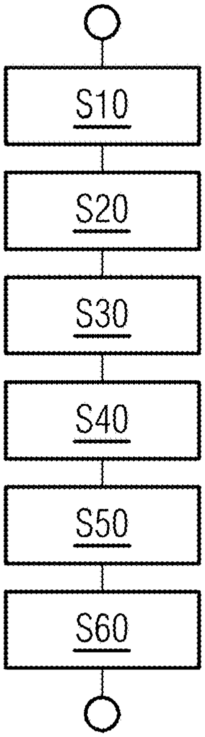
FIG. 5 depicts a schematic representation of an example of a flow chart of the method.

FIG. 5 is a schematic flow chart of a method. The method is provided for aligning a medical instrument on the body of a patient in a patient tunnel 16 of a magnetic resonance imaging device 1. Herein, the medical instrument 70 may be the instrument 70 in FIG. 3 or also the medical instrument in FIG. 4.

In act S10, a trajectory 101 for the medical instrument 70 in a patient 100 is ascertained for a predetermined interventional procedure. This may be carried out by the controller 23 of the magnetic resonance imaging device or by or with the support of a separate planning system by a magnetic resonance recording of the patient 100. Herein, starting from the target object 103, a straight line to the surface or skin of the patient 100 is ascertained which allows access to the target object 103 while bypassing sensitive tissue or blood vessels and obstacles such as bones.

In act S20, the controller identifies the entry point on the patient 100 and an impact point or point of intersection on the display 100. The ascertained trajectory 101 is defined through an entry point on the surface of the patient 100 and an alignment in two spatial directions, which are determined in a coordinate system of the underlying magnetic resonance recording. If the magnetic resonance recording for ascertaining was not captured immediately before the procedure with the unchanged position of the patient 100, the current position of the patient 100 may first be acquired with a further magnetic resonance recording or by a 3D recording of the body surface and the coordinate systems aligned with one another by a coordinate transformation to define a straight line through the trajectory 101 in the position of the patient 100 for the interventional procedure.

The entry point may then be identified in a real-time magnetic resonance recording using the surgeon's finger or a magnetic resonance-active marker.

In act S30, the user or the surgeon positions the medical instrument 70 at the entry point on the patient 100. For this purpose, the user moves the tip of the medical instrument 70 to the entry point, which, for example, was marked with the finger or a magnetic resonance-active substance in a previous act under real-time mapping with the magnetic resonance imaging device 1.

In act S40, a point of intersection of the ascertained trajectory 101 in the coordinate system of the magnetic resonance imaging device is determined, for example, after the aforementioned coordinate transformation for aligning the coordinate systems, with the wall of the patient tunnel 16 or the display 80. Depending on the size of the display 80 and the position of the patient 100, the display 80 may be moved along the recess or the patient 100 may be moved on the patient couch until the display 80 is at the point of intersection or the trajectory has a point of intersection with the display 80.

In act S50, the controller marks the impact point or the point of intersection of the trajectory 101 with the display 80 by outputting a marking at the corresponding location of the point of intersection on the display 80.

In act S60, the surgeon aligns the distal end of the medical instrument with the marking.

In the embodiment in FIG. 3, in which the medical instrument has a luminous pointer that projects a light marking along the elongate shape or longitudinal direction of the medical instrument in the distal direction, the user brings the light marking of the luminous pointer into coincidence with the marking on the display by tilting the distal end.

In the embodiment of the medical instrument 70 in FIG. 4, the surgeon receives an image from the camera 77 displayed on a screen, e.g., outside the patient tunnel 16. Due to the alignment along the longitudinal axis of the medical instrument 70, in the direction away from the patient 100, the medical instrument 70 is aligned precisely along the trajectory when the marking on the display 70 is centered in the image captured by the camera. Herein, the surgeon changes the inclination of the medical instrument until central alignment in the camera image is achieved.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance imaging device for an interventional procedure, the magnetic resonance imaging device comprising:

a field magnet with a patient tunnel for receiving a patient, wherein the patient tunnel has a recess within an inner wall of the patient tunnel, wherein the patient tunnel extends in an axial direction, and wherein the recess extends at least partially along an inner circumference of the patient tunnel;

a display arranged along a circumferential direction in the recess of the patient tunnel; and a gradient coil divided into a first section and a second section along the patient tunnel in the axial direction, wherein the recess is arranged between the first section and the second section of the gradient coil.

2. The magnetic resonance imaging device of claim 1, wherein the display has electromagnetic shielding configured to reduce interference with magnetic resonance signals caused by emissions from the display, interference with the display caused by magnetic and/or electromagnetic fields during magnetic resonance mapping, or a combination thereof.

3. The magnetic resonance imaging device of claim 1, wherein the display has electromagnetic shielding configured to reduce interference with magnetic resonance signals caused by emissions from the display, interference with the display caused by magnetic and/or electromagnetic fields during magnetic resonance mapping, or a combination thereof.

4. The magnetic resonance imaging device of claim 1, further comprising:

a medical instrument having a proximal end and a distal end, wherein an optical image capturing apparatus is positioned at the distal end, wherein the optical image capturing apparatus is configured to capture the display at least partially in a map.

5. The magnetic resonance imaging device of claim 4, wherein the medical instrument comprises a luminous pointer that projects a light marking in a distal direction, and wherein the distal end of the medical instrument is configured to be aligned during the interventional procedure by bringing the light marking of the luminous pointer into coincidence with a marking on the display.

6. The magnetic resonance imaging device of claim 5, wherein the marking on the display relates to an impact point of a trajectory with the display, wherein the trajectory is a path of the medical instrument for the interventional procedure along a straight line from an entry point on a surface of the patient to a target.

7. The magnetic resonance imaging device of claim 4, wherein the medical instrument is a biopsy needle or an instrument for brachytherapy.

8. A medical instrument for an interventional procedure, the medical instrument comprising:

an elongate shape having a proximal end and a distal end; and an optical image capturing apparatus positioned at the distal end, wherein the optical image capturing apparatus is configured to capture a display of a magnetic resonance imaging device at least partially in a map, and wherein the display is arranged along a circumferential direction in a recess of a patient tunnel of the magnetic resonance imaging device.

9. The medical instrument of claim 8, wherein the medical instrument comprises a luminous pointer that projects a light marking in a distal direction, and wherein the distal end of the medical instrument is configured to be aligned during the interventional procedure by bringing the light marking of the luminous pointer into coincidence with a marking on the display.

10. The medical instrument of claim 9, wherein the marking on the display relates to an impact point of a trajectory with the display, wherein the trajectory is a path of the medical instrument for the interventional procedure along a straight line from an entry point on a surface of a patient to a target.

11. The medical instrument of claim 8, wherein the medical instrument is a biopsy needle or an instrument for brachytherapy.

12. A method for aligning a medical instrument on a body of a patient in a patient tunnel of a magnetic resonance imaging device having a display arranged along a circumferential direction in a recess of the patient tunnel, wherein the medical instrument has an elongate shape having a proximal end and a distal end, and wherein the method comprises:

ascertaining a trajectory for the medical instrument in the patient for a predetermined interventional procedure;

identifying an entry point on the patient and an impact point on the display of the magnetic resonance imaging device, wherein the entry point and the impact point define a straight line through the trajectory in a position of the patient for the predetermined interventional procedure;

positioning the medical instrument at the entry point by a user;

marking the impact point by outputting a marking on the display; and aligning the distal end of the medical instrument with the marking.

13. The method of claim 12, wherein the medical instrument comprises an optical image capturing apparatus positioned at the distal end, wherein the optical image capturing apparatus captures the display of the magnetic resonance imaging device at least partially in a map, and wherein the aligning of the distal end of the medical instrument comprises bringing the marking on the display by the user to a predetermined position in the map captured by the optical image capturing apparatus by tilting the medical instrument.

14. The method of claim 12, wherein the medical instrument comprises a luminous pointer that projects a light marking in a distal direction, and wherein the aligning of the distal end of the medical instrument comprises bringing the light marking of the luminous pointer by the user into coincidence with the marking on the display.

15. The method of claim 12, wherein the medical instrument is a biopsy needle or an instrument for brachytherapy.

* * * * *